United States Patent
Sugimoto

(10) Patent No.: US 10,647,642 B2
(45) Date of Patent: May 12, 2020

(54) METHOD FOR PRODUCING FLUORINATED HYDROCARBONS

(71) Applicant: ZEON CORPORATION, Chiyoda-ku, Tokyo (JP)

(72) Inventor: Tatsuya Sugimoto, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

(21) Appl. No.: 16/492,283

(22) PCT Filed: Mar. 13, 2018

(86) PCT No.: PCT/JP2018/009805
§ 371 (c)(1),
(2) Date: Sep. 9, 2019

(87) PCT Pub. No.: WO2018/173863
PCT Pub. Date: Sep. 27, 2018

(65) Prior Publication Data
US 2019/0389790 A1    Dec. 26, 2019

(30) Foreign Application Priority Data

Mar. 22, 2017 (JP) ................................ 2017-056294

(51) Int. Cl.
*C07C 17/361* (2006.01)
*C07C 19/08* (2006.01)
*B01J 23/04* (2006.01)

(52) U.S. Cl.
CPC ............ *C07C 17/361* (2013.01); *C07C 19/08* (2013.01); *B01J 23/04* (2013.01)

(58) Field of Classification Search
CPC ....... C07C 17/361; C07C 19/08; C07C 51/60; C07C 41/16; C07C 43/04; C07C 53/42; C07C 53/40; C07C 17/16; B01J 23/04
See application file for complete search history.

(56) References Cited

U.S. PATENT DOCUMENTS

| | | | |
|---|---|---|---|
| 2,550,953 A | 5/1951 | Barrick | |
| 6,054,606 A | 4/2000 | Irie et al. | |
| 9,738,578 B2 * | 8/2017 | Sugimoto | ............. B01J 31/146 |
| 2011/0068086 A1 | 3/2011 | Suzuki et al. | |
| 2012/0283469 A1 | 11/2012 | Erman et al. | |
| 2017/0174588 A1 | 6/2017 | Sugimoto | |
| 2018/0215688 A1 | 8/2018 | Sugimoto | |

FOREIGN PATENT DOCUMENTS

| | | |
|---|---|---|
| JP | S5946251 A | 3/1984 |
| JP | H10109034 A | 4/1998 |
| JP | 2009292749 A | 12/2009 |
| JP | 2012250961 A | 12/2012 |
| JP | 2014522390 A | 9/2014 |
| JP | 2017122069 A | 7/2017 |
| JP | 2017155005 A | 9/2017 |
| WO | 2009123038 A1 | 10/2009 |
| WO | 2015122386 A1 | 8/2015 |
| WO | 2017022571 A1 | 2/2017 |

OTHER PUBLICATIONS

James F. Norris et al., The Reactivity of Atoms and Groups in Organic Compounds. XII. The Preparation and Properties of Mixed Aliphatic Ethers With Special Reference to Those Containing the Tert.-Butyl Radical, Journal of the American Chemical Society, May 1932, pp. 2088 to 2100, vol. 54.

James H. Clark et al., Reactions of potassium fluoride in glacial acetic acid with chlorocarboxylic acids, amides, and chlorides. The effect of very strong hydrogen bonding on the nucleophilicity of the fluoride anion, Journal of the Chemical Society, Dalton Transactions, 1975, pp. 2129 to 2134, issue 20.

Jun. 5, 2018, International Search Report issued in the International Patent Application No. PCT/JP2018/009805.

Kimura Chikai et al., Alkylation of Butyl Alcohols by Dialkyl Sulfates Using Phase Transfer Catalysis, Journal of Japan Oil Chemists' Society, 1982, pp. 960 to 962, vol. 31, issue 11.

(Continued)

Primary Examiner — Jafar F Parsa
(74) Attorney, Agent, or Firm — Kenja IP Law PC

(57) ABSTRACT

Provided is a method for industrially advantageously producing a fluorinated hydrocarbon (3). The disclosed method for producing a fluorinated hydrocarbon represented by formula (3) includes bringing into contact, in a hydrocarbon-based solvent, a secondary or tertiary ether compound represented by formula (1) below with an acid fluoride represented by formula (2) in the presence of lithium salt or sodium salt (in the formulae, $R^1$ and $R^2$ each represent a $C_{1-3}$ alkyl, and $R^1$ and $R^2$ may be bonded to each other to form a ring structure; $R^3$ represents a hydrogen atom, methyl, or ethyl; and $R^4$ and $R^5$ each represent methyl or ethyl).

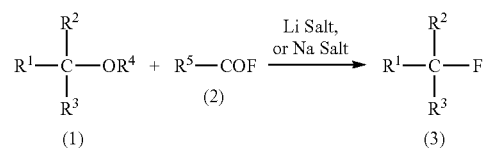

5 Claims, No Drawings

(56) References Cited

OTHER PUBLICATIONS

Manabe Kei, Hardness and softness of acid and base, Chemistry & Education, 2008, pp. 400 to 401, vol. 56.
N. O. Calloway, Reactions in the Presence of Metallic Halides. II. The Behavior of Fluorides and the Reactivity of the Halogens, Journal of the American Chemical Society, Aug. 1937, pp. 1474 to 1479, vol. 59.
Suzuki Zennosuke et al., An Acid-catalyzed Reaction of Methyl Ethers with Acetyl Fluoride. Syntheses of 1-Fluorobicyclo[2.2.2]octanes, Bulletin of the Chemical Society of Japan, 1968, pp. 1724 to 1725, vol. 41, No. 7.
The Chemical Society of Japan, Chemistry handbook Basic part, 20012, pp. II-331 to II-332, revised edition 5.
Sep. 24, 2019, International Preliminary Report on Patentability issued in the International Patent Application No. PCT/JP2018/009805.

* cited by examiner

METHOD FOR PRODUCING FLUORINATED HYDROCARBONS

TECHNICAL FIELD

Disclosed is a method for producing fluorinated hydrocarbons useful as, for example: plasma reaction gases used in plasma etching, plasma chemical vapor deposition (plasma CVD) and the like; fluorine-containing medical intermediates; and hydrofluorocarbon-based solvents. Highly purified fluorinated hydrocarbons are suitable as plasma etching gases, plasma CVD gases and the like, in particular, in the field of producing semiconductor devices using plasma reaction.

BACKGROUND

Recently, miniaturization of semiconductor production techniques has increasingly progressed, in such a way that the state-of-the-art process has adopted generations having wiring widths of the order of 20 nm and further 10 nm. Miniaturization goes with the enhancement of the technical difficulty in the miniaturization processing, and technical developments have been progressed from various aspects of approach, with respect to the materials, apparatuses, processing methods and others to be used.

Under such circumstances, the present applicant has also developed a dry etching gas capable of coping with the state-of-the-art dry etching process, and has discovered that saturated fluorinated hydrocarbons having small number of fluorine atoms such as 2-fluorobutane have performances surpassing monofluoromethane being used in etching of silicon nitride films (see, for example, Patent Literature 1).

Several methods for producing 2-fluorobutane have hitherto been known. For example, Patent Literature 2 describes a production of 2-fluorobutane in a yield of 46%, by bringing N,N'-diethyl-3-oxo-methyltrifluoropropylamine as a fluorinating agent into contact with 2-butanol. Patent Literature 3 discloses that the generation of fluorinated sec-butyl fluoride was confirmed by bringing sulfur hexafluoride into contact with a sec-butyl lithium solution in a cyclohexane/n-hexane mixed solvent. Patent Literature 4 describes the preparation of 2-fluorobutane by hydrogenation of 2-fluorobutadiene in the presence of a catalyst. Non-Patent Literature 1 also discloses a method for preparing monofluorinated hydrocarbons having a cyclic structure by acting acetyl fluoride as a fluorinating agent to ether compounds having a cyclic structure such as adamantyl methyl ether and cyclohexyl methyl ether in the presence of a catalyst such as boron trifluoride phosphoric acid complex or zinc fluoride.

CITATION LIST

Patent Literature

PTL 1: WO2009123038
PTL 2: JPS5946251A
PTL 3: JP2009292749A
PTL 4: U.S. Pat. No. 2,550,953B

Non-Patent Literature

NPL 1: Bulletin of the Chemical Society of Japan, Vol. 41, 1724 (1968)

SUMMARY

Technical Problem

As described above, several methods for producing 2-fluorobutane have hitherto been known.

However, the fluorinating agent used in the method described in Patent Literature 2 is extremely high in price, and the method described in Patent Literature 3 uses alkyl lithium, which involves a risk of ignition. I tried a reaction in the absence of a solvent, according to the description of Non-Patent Literature 1, and have found that by-produced is a large amount of an acetic acid alkyl ester, a by-product, in which the methyl group portion of a methyl alkyl ether is substituted with an acetyl group derived from the fluorinating agent.

As can be seen from the above, it has been difficult to apply the conventional methods for producing 2-fluorobutane from the viewpoint of the industrial productivity.

Under such circumstances as described above, I have reported, in WO2015/122386, that a fluorinated hydrocarbons such as 2-fluorobutane is obtained in a good yield while the production of acetic acid alkyl esters, by-products, is being suppressed, when an alkyl ether compound of a secondary alcohol such as sec-butyl methyl ether or sec-butyl ethyl ether is used as a starting material, acetyl fluoride is used as a fluorinating agent, and an ether complex of boron trifluoride is used as a catalyst, in a hydrocarbon solvent.

However, a subsequent investigation has revealed that when a fluorinated carbon such as 2-fluorobutane is brought into contact with a Lewis acid compound (for example, boron trifluoride), 2-fluorobutane is partially decomposed into hydrogen fluoride and olefins such as butenes, and thus it has been found that an improvement is necessary. It has also been found that when an ether complex of boron trifluoride is used, the ether compound constituting the complex is liberated in the reaction system, the liberated ether acts as an impurity for the fluorinated hydrocarbon as the target compound, and the liberated ether sometimes causes a load on the purification of the target compound, depending on the type of the liberated ether. Further, boron trifluoride as a catalyst needs to be readily separated from the reaction liquid.

It could therefore be helpful to provide a method for industrially advantageously producing a fluorinated hydrocarbon such as 2-fluorobutane.

Solution to Problem

I have made a diligent study on the reaction between an alkyl ether compound such as secondary or tertiary alcohol and acetyl fluoride when both are brought into contact with each other in a hydrocarbon-based solvent. As a result, I have discovered that an industrially-inexpensive lithium salt or sodium salt may be contained as a catalyst in a reaction system, so that: (a) no ether compound (no impurity) is by-produced unlike when using an ether complex of boron trifluoride as a catalyst, and thus a substantially colorless reaction liquid is obtained; (b) the catalyst residue is readily separated from the reaction liquid, which thus allows for industrially advantageously producing the targeted fluorinated hydrocarbon.

Thus, the following methods (i) to (v) for producing the fluorinated hydrocarbon represented by formula (3) are provided.

(i) A method for producing a fluorinated hydrocarbon represented by formula (3) below, wherein an ether compound represented by formula (1) and an acid fluoride represented by formula (2) below are brought into contact with each other in a hydrocarbon-based solvent, in the presence of lithium salt or sodium salt,

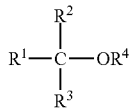
(1)

(in formula (1) above, $R^1$ and $R^2$ each independently represent an alkyl group having 1 to 3 carbon atoms, $R^3$ represents a hydrogen atom, a methyl group or an ethyl group, and $R^4$ represents a methyl group or an ethyl group; and $R^1$ and $R^2$ may be bonded to each other to form a cyclic structure),

(2)

(in formula (2) above, $R^5$ represents a methyl group or an ethyl group),

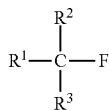
(3)

(in formula (3) above, $R^1$ to $R^3$ represent the same meanings as described above).

(ii) The production method according to (i), wherein the lithium salt or the sodium salt is inorganic acid salt.

(iii) The production method according to (i) or (ii), wherein an ether compound represented by formula (1) above is sec-butyl methyl ether or t-butyl methyl ether.

(iv) The production method according to any one of (i) to (iii), wherein the acid fluoride represented by formula (2) is acetyl fluoride.

(v) The production method according to any one of (i) to (iv), wherein the fluorinated hydrocarbon represented by formula (3) is 2-fluorobutane.

Advantageous Effect

In the disclosed method, an industrially-inexpensive lithium salt or sodium salt may be contained as a catalyst in the reaction system, so that: no ether compound (impurities) is by-produced unlike when using an ether complex of boron trifluoride as a catalyst; and further, the catalyst residue is readily separated from the reaction liquid in the post-treatment step, to thereby obtain a substantially colorless reaction liquid, which thus allows for industrially advantageously producing the targeted fluorinated hydrocarbon.

DETAILED DESCRIPTION

Hereinafter, the disclosed method is described in detail.
The disclosed method is for producing a fluorinated hydrocarbon represented by formula (3) below (which may be hereinafter referred to as "fluorinated hydrocarbon (3)"), by bringing into contact an ether compound represented by formula (1) below (which may be hereinafter referred to as "ether compound (1)") with an acid fluoride represented by formula (2) (which may be hereinafter referred to as "acid fluoride (2)"), in a hydrocarbon-based solvent, in the presence of lithium salt or sodium salt.

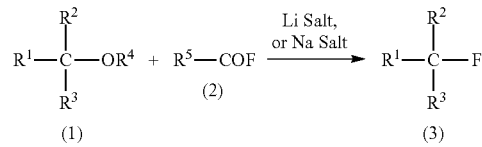

[Ether Compound (1)]

The starting material used in the disclosed method is an ether compound (1).

In formula (1), $R^1$ and $R^2$ each independently represent an alkyl group having 1 to 3 carbon atoms.

Examples of the alkyl groups having 1 to 3 carbon atoms represented by $R^1$ and $R^2$ may include: a methyl group, an ethyl group, an n-propyl group, and an isopropyl group.

$R^1$ and $R^2$, which may be bonded to each other to form a cyclic structure, are preferably not forming a cyclic structure.

Examples of the cyclic structure formed by $R^1$ and $R^2$ which are bonded to each other, together with carbon atoms to which $R^1$ and $R^2$ are boded, include: a cyclopropane ring; a cyclobutane ring; a cyclopentane ring; a cyclohexane ring; and a cycloheptane ring.

$R^3$ represents a hydrogen atom, a methyl group or an ethyl group.

$R^4$ represents a methyl group or an ethyl group.

Preferred examples of the ether compound (1) are those having preferably 4 to 7 carbon atoms, more preferably 4 or 5 carbon atoms in total in $R^1$ to $R^3$.

Specific examples of the ether compound (1) include: methyl ethers such as sec-butyl methyl ether, t-butyl methyl ether, cyclobutyl methyl ether, 2-pentyl methyl ether, 3-pentyl methyl ether, 2-methyl-2-butyl methyl ether, and cyclopentyl methyl ether; and ethyl ethers such as sec-butyl ethyl ether, t-butyl ethyl ether, cyclobutyl ethyl ether, 2-pentyl ethyl ether, 3-pentyl ethyl ether, 2-methyl-2-butyl ethyl ether, and cyclopentyl ethyl ether.

Of these, alkyl methyl ether compounds having 4 or 5 carbon atoms, such as: sec-butyl methyl ether, t-butyl methyl ether, 2-pentyl methyl ether; and alkyl ethyl ether compounds having 4 or 5 carbon atoms, such as: sec-butyl ethyl ether, t-butyl ethyl ether, and 2-pentyl ethyl ether are preferred in terms of efficient production of the target product and easy availability of the raw materials, with sec-butyl methyl ether, sec-butyl ethyl ether, t-butyl methyl ether, 2-pentyl methyl ether being further preferred, and sec-butyl methyl ether, t-butyl methyl ether being still further preferred, in terms of efficient production of the target product.

Examples of the method for producing the ether compound (1) include, without being particularly limited to: heretofore known methods such as a method described in Journal of Japan Oil Chemists' Society (Yukagaku), Vol. 31, p. 960 (1982), and a method described in Journal of American Chemical Society, Vol. 54, 2088 (1932) may be employed. In the former method, the corresponding alcohol is brought into contact with a sulfuric acid ester in the presence of a phase-transfer catalyst such as a 50% concentration of sodium hydroxide and tetraalkylammonium salt. In the latter method, the corresponding anhydrous alcohol is brought into contact with metallic sodium, and then brought into contact with an alkyl bromide or an alkyl iodide to produce an ether compound.

[Acid Fluoride (2)]

The disclosed method uses the acid fluoride (2) as a fluorinating agent.

In formula (2), $R^5$ is a methyl group or an ethyl group.

The acid fluoride (2) is specifically acetyl fluoride or propionyl fluoride, with acetyl fluoride being preferred in terms of efficient production of the target product.

The acid fluoride (2) is a heretofore known substance, can be produced by a heretofore known method, and is available. The acid fluoride (2) can be produced according to the method described in, for example, "Journal of Chemical Society Dalton Transaction, 2129 (1975)", or "Journal of American Chemical Society, Vol. 59, 1474 (1937)". In the former method, potassium fluoride is dissolved in acetic acid, acetyl chloride or propionyl chloride is added under heating, and generated acetyl fluoride or propionyl fluoride is collected. In the latter method, sodium hydrogen difluoride is dissolved in acetic anhydride, acetyl chloride is added, and the generated acetyl fluoride is collected.

The amount of the acid fluoride (2) used is generally 7 equivalents or more, preferably 0.8 equivalents or more, more preferably 0.9 equivalents or more, and generally 3.0 equivalents or less, preferably 2.5 equivalents or less, more preferably 2.0 equivalents or less, in relation to 1 equivalent of the ether compound (1). When the amount of the acid fluoride (2) used falls within such a range, the productivity is excellent, and the post-treatment or the purification process is not cumbersome, which is preferable.

Of the acid fluorides (2), acetyl fluoride acts as a fluorinating agent and then is converted into methyl acetate, when a methyl ether compound is used as the ether compound (1). Acetyl fluoride is converted into ethyl acetate when an ethyl ether compound is used as the ether compound (1).

Of the acid fluorides (2), propionyl fluoride acts as a fluorinating agent and then is converted into methyl propionate, when a methyl ether compound is used as the ether compound (1). Propionyl fluoride is converted into ethyl propionate when an ethyl ether compound is used as the ether compound (1).

[Lithium Salt/Sodium Salt]

In the disclosed method, the ether compound (1) is brought into contact with the acid fluoride (2), in the presence of lithium salt or sodium salt.

Specific examples of the lithium salt include: inorganic acid lithium salt such as lithium fluoride, lithium chloride, lithium bromide, lithium iodide, lithium phosphate, lithium nitrate, lithium tetrafluoroborate, lithium carbonate, lithium sulfate, lithium hexafluorophosphate, lithium sulphamate; and organic acid lithium salt such as lithium formate, lithium acetate, lithium oxalate, lithium methanesulfonate, lithium p-toluenesulfonate, lithium trifluoroacetate, lithium maleate, lithium fumarate, lithium itaconate, lithium trifluoromethanesulfonate, lithium nonafluorobutansulfonate.

Specific examples of the sodium salt include: inorganic acid sodium salt such as sodium fluoride, sodium chloride, sodium bromide, sodium iodide, sodium phosphate, sodium nitrate, sodium tetrafluoroborate, sodium carbonate, sodium sulfate, sodium hexafluorophosphate, sodium hydrogencarbonate, sodium hydrogen sulfite, sodium sulfite, sodium thiosulfate, sodium hydrogen difluoride, sodium sulphamate; and organic acid sodium salt such as sodium formate, sodium acetate, sodium oxalate, sodium methanesulfonate, sodium p-toluenesulfonate, sodium trifluoroacetate, sodium heptafluorobutyrate, sodium maleate, sodium fumarate, sodium itaconate, sodium trifluoromethanesulfonate, sodium nonafluorobutansulfonate.

These lithium salts and sodium salts may each be used alone or in combination of two or more kinds.

Of these, inorganic acid lithium salt such as lithium fluoride, lithium chloride, lithium bromide, lithium iodide, lithium phosphate, lithium nitrate, lithium tetrafluoroborate, lithium carbonate, lithium sulfate, lithium hexafluorophosphate, lithium sulphamate; and inorganic acid sodium salt such as sodium fluoride, sodium chloride, sodium bromide, sodium iodide, sodium phosphate, sodium nitrate, sodium tetrafluoroborate, sodium carbonate, sodium sulfate, sodium hexafluorophosphate, sodium hydrogencarbonate, sodium hydrogensulfite, sodium sulfite, sodium thiosulfate, sodium hydrogen difluoride, sodium sulphamate are preferred in terms of more readily obtaining the effect of the disclosure, with lithium fluoride, with lithium chloride, lithium bromide, lithium iodide, lithium phosphate, lithium nitrate, lithium tetrafluoroborate, lithium carbonate, sodium fluoride, sodium chloride, sodium bromide, sodium iodide, sodium phosphate, sodium nitrate, sodium tetrafluoroborate, sodium carbonate, sodium sulfate, sodium hexafluorophosphate, sodium hydrogencarbonate being more preferred in terms of economy, availability, and efficient production of the target product.

The amount of lithium salt or sodium salt used is preferably 0.005 equivalents or more, more preferably 0.01 equivalent or more, and preferably 0.3 equivalent or less, more preferably 0.2 equivalents or less, in terms of the lithium content in the lithium salt (or the sodium content in the sodium salt), in relation to 1 equivalent of the ether compound (1) as the raw material.

When the amount of the lithium salt or the sodium salt is too small, the reaction fails to complete, which may leave residue of the ether compound (1) as the raw material. When the lithium salt or the sodium salt is added too much, which is economically disadvantageous, the solid concentration of the content is increased, making the stirring difficult and potentially causing some troubles, for example, in post-treatment.

[Hydrocarbon-Based Solvent]

The disclosed method uses a hydrocarbon-based solvent as a reaction solvent. The use of a hydrocarbon-based solvent as a reaction solvent provides excellent effects as disclosed herein. Without any solvent, lithium salt or sodium salt as the catalyst are brought into excessive contact with the ether compound (1) as the raw material or with the generated fluorinated hydrocarbon (3) as the target, which may potentially result in increased generation of byproducts such as olefin.

As the hydrocarbon-based solvent used in the disclosed method, in consideration of the load to be applied in the purification process (distillation purification), preferably used is a compound having a boiling point higher by 25° C. or more than the boiling point of the fluorinated hydrocarbon (3) as the product.

Specific examples of such a hydrocarbon-based solvent include: hydrocarbon-based solvents having 5 carbon atoms such as n-pentane and cyclopentane; hydrocarbon-based solvents having 6 carbon atoms such as n-hexane, 2-methylpentane, 3-methylpentane, 2,2-dimethylbutane, 2,3-dimethylbutane, cyclohexane and methylcyclopentane; hydrocarbon-based solvents having 7 carbon atoms such as n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane, cycloheptane and toluene; hydrocarbon-based solvents having 8 carbon atoms such as n-octane, 4-methylheptane, 2-methylheptane, 3-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane, 2,3,3-trim ethyl pentane, 2,3,4-trimethylpentane, 2-methyl-3-ethylpentane, 3-methyl-3-ethylpentane, cyclooctane, ethyl benzene and xylene. When the hydrocarbon-based solvents are mutually in a relationship of being isomers, a mixture of composed such isomers may also be used as a hydrocarbon-based solvent.

From the viewpoint of easiness in handling, more preferable among these are: hydrocarbon-based solvents having 6 carbon atoms such as n-hexane, 2-methylpentane, 3-methylpentane, 2,2-dimethylbutane, 2,3-dimethylbutane, cyclohexane and methylcyclopentane; and hydrocarbon-based solvents having 7 carbon atoms such as n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane, cycloheptane and toluene.

The amount of each of these hydrocarbon-based solvents used is generally 1 ml or more, preferably 2 ml or more, more preferably 2.5 ml or more, and generally 10 ml or less, preferably 5 ml or less, and more preferably 3 ml or less, in relation to 1 g of the ether compound (1) to be the raw material. When the amount of the hydrocarbon-based solvent used is too small, the amount of the acetic acid alkyl ester produced as a by-product is increased. On the other hand, when the amount of the hydrocarbon-based solvent used is too large, a long period of time may be required to complete the reaction, or the treatment of the waste liquid during post-treatment may be cumbersome.

[Reaction]

An exemplary method of bringing the ether compound (1) into contact with the acid fluoride (2) may include: charging, in a reactor, the ether compound (1) as the raw material and a hydrocarbon-based solvent; cooling the reactor to a predetermined temperature (of, for example, 0° C. or higher and 10° C. or lower) and then adding the acid fluoride (2) as a fluorinating agent, and further adding lithium salt or sodium salt as a catalyst; and thereafter keeping stirring the content while holding the content at a predetermined temperature.

The lithium salt or the sodium salt as a catalyst may be added all at once, or divided in batches to be added a plurality of times such as twice or three times.

The temperature (reaction temperature) at which the ether compound (1) and the acid fluoride (2) are brought into contact with each other is preferably 0° C. or higher, more preferably 10° C. or higher, and preferably 40° C. or lower, more preferably 30° C. or lower. The aforementioned temperature range allows for properly regulating the reaction rate while achieving excellent productivity, and suppressing volatilization loss of the produced fluorinated hydrocarbon (3).

The reaction time depends on the combination of the ether compound (1) to be the raw material, the acid fluoride (2) and the hydrocarbon-based solvent or on the reaction scale, but is generally 3 hours or longer and 24 hours or shorter, preferably 5 hours or longer and 20 hours or shorter, and more preferably 5 hours or longer and 12 hours or shorter.

When the reaction time is too short, the reaction is not completed, leaving unreacted raw materials or the acid fluoride (2) functioning as the fluorinating agent remain in a large amount, which may make the post-treatment cumbersome. On the other hand, when the reaction time is too long, some troubles are likely to be caused in which the reaction may excessively occur, increasing the production amount of the alkyl ester as a by-product.

After the completion of reaction, the reaction liquid most likely contains catalyst residue that has settled therein. The reaction liquid may be filtered to separate lithium fluoride (or sodium fluoride) along with catalyst residue, to thereby recover the reaction liquid. Further, in order to remove a trace amount of fluorinated hydrogen generated in a reaction, a reaction reagent (hydrogen fluoride remover) for removing hydrogen fluoride such as sodium fluoride may preferably be added to the reaction liquid and stirred, before filtering the reaction liquid.

The disclosed method uses a solid catalyst (lithium salt or sodium salt), which allows for readily separating and removing the catalyst through filtration without needing any troublesome operation such as neutralization.

Thereafter, the filtrate thus obtained may be distilled by means of a distillation column, to thereby isolate the fluorinated hydrocarbon (3) as the target product.

When the fluorinated hydrocarbon (3) is desired to have still higher purity, a rectification may be again performed.

In the manner as described above, the fluorinated hydrocarbon (3) can be obtained.

According to the disclosed method, the reaction system includes, as a catalyst, industrially-inexpensive lithium salt or sodium salt, and thus no ether compound (impurity) is by-produced unlike when using an ether complex of boron trifluoride as a catalyst, and a substantially colorless reaction liquid can be obtained. Further, the catalyst residue is readily separated from the reaction liquid, which allows for industrially advantageously producing the targeted fluorinated hydrocarbon.

Specific examples of the fluorinated hydrocarbon (3) obtained by the production method of the present invention include: 2-fluorobutane, t-butyl fluoride, 2-fluoropentane, 3-fluoropentane, 2-methyl-2-fluorobutane, cyclobutyl fluoride, cyclopentyl fluoride and cyclohexyl fluoride, Of these, 2-fluorobutane, 2-fluoropentane, and 2-fluoro-2-methylpropane are preferred, with 2-fluorobutane being particularly preferred, in terms of the easy availability of the raw materials.

EXAMPLES

Hereinafter, by way of Examples, the present invention is described in further details, but the scope of the present invention is not limited by following Examples. Note that "%" represents "mass %" unless otherwise specified.

The analytical conditions adopted hereinafter are as follows.

Gas Chromatography Analysis (GC Analysis)

Apparatus: HP-6890 (manufactured by Agilent Technologies, Inc.)

Column: Inert Cap-1 (manufactured by GL Sciences Inc., length: 60 m, inner diameter: 0.25 mm, film thickness: 1.5 μm)

Column temperature: Maintained at 40° C. for 10 minutes, subsequently, increased to 240° C. at a rate of 20° C./min., and then maintained at 240° C. for 10 minutes Injection temperature: 200° C.

Carrier gas: Nitrogen

Split ratio: 100/1

Detector: FID

Gas Chromatography Mass Analysis (GC-MS)

GC section: HP-6890 (manufactured by Agilent Technologies, Inc.)

Column: Inert Cap-1 (manufactured by GL Sciences Inc., length: 60 m, inner diameter: 0.25 mm, film thickness: 1.5 µm)

Column temperature: Maintained at 40° C. for 10 minutes, subsequently, increased to 240° C. at a rate of 20° C./min., and then maintained at 240° C. for 10 minutes MS section: 5973 NETWORK (manufactured by Agilent Technologies, Inc.)

Detector: EI-type (acceleration voltage: 70 eV)

[Production Example 1] Production of sec-Butyl Methyl Ether

In a 500 mL volume eggplant flask with a stirring bar placed therein, 360 mL of 2-butanol and 37.3 g of flaky potassium hydroxide (manufactured by Aldrich Corporation, purity: approximately 90%) were charged, and the resulting mixture was stirred for approximately 2.5 hours at 50° C. When potassium hydroxide was dissolved to produce a uniform solution, the heating was once ceased. To the resulting uniform solution, 84.4 g of iodomethane was added, and the resulting mixture was stirred at 50° C. for a little over 3 hours in a state of being equipped with a Dimroth condenser. After the completion of the reaction, the reaction liquid was cooled to room temperature (approximately 25° C.; hereinafter the same) and the supernatant solution was analyzed by gas chromatography (which may be hereinafter referred to as "GC"), to find that iodomethane was virtually consumed, and the supernatant solution contained 2-butanol and sec-butyl methyl ether as the target.

Potassium iodide was filtered off from the content in the eggplant flask, to obtain a filtrate. The filtered-off potassium iodide was dissolved in a small amount of water to separate the upper layer of an organic phase, and the separated organic phase was mixed with the foregoing filtrate, to thereby obtain a filtrate mixture.

The obtained filtrate mixture was charged in a distillation still, and distilled by using a KS-type rectifier (manufactured by TOKA SEIKI Co., Ltd., column length: 30 cm, column packing material: Helipack No. 1). The fraction of the column top temperature of 55-56° C. was collected, the water azeotropically boiled and distilled was separated by using a separating funnel, the obtained distillate was dried with the molecular sieves 4A, and thus 38 g of sec-butyl methyl ether was obtained (yield: 72%).
GC-MS (EI-MS): m/z 73, 59, 41, 29

[Production Example 2] Production of sec-Butyl Ethyl Ether

In a 500 mL volume eggplant flask with a stirring bar placed therein, 240 mL of 2-butanol and 24.8 g of flaky potassium hydroxide (manufactured by Aldrich Corporation, purity: approximately 90%) were charged, and the resulting mixture was stirred for 3 hours at 50° C. When potassium hydroxide was dissolved to produce a uniform solution, the heating was once ceased. To the resulting uniform solution, 43 g of ethyl bromide was added, and the mixture was stirred at 70° C. for a little over 4 hours in a state of being equipped with a Dimroth condenser. The reaction mixture was cooled to room temperature and the supernatant solution was analyzed by GC, to find that ethyl bromide was virtually consumed, and the supernatant solution contained 2-butanol and sec-butyl ethyl ether as the target.

Potassium bromide was filtered off from the content in the eggplant flask, to obtain a filtrate. The filtered-off potassium bromide was dissolved in a small amount of water, the upper layer of an organic phase was separated, and the separated organic phase was mixed with the foregoing filtrate mixture to obtain a filtrate mixture.

The obtained filtrate mixture was charged in a distillation still, and distilled by using a KS-type rectifier (manufactured by TOKA SEIKI Co., Ltd., column length: 30 cm, column packing material: Helipack No. 1). The fraction of the column top temperature of 68-69° C. was collected, the water azeotropically boiled and distilled was separated by using a separating funnel, the obtained distillate was dried with the molecular sieves 4A, and thus 31 g of sec-butyl ethyl ether was obtained (yield: 51%).
GC-MS (EI-MS): m/z 87, 73, 59, 45

[Production Example 3] Production of 2-Pentyl Methyl Ether

In a 500 mL volume eggplant flask equipped with a Dimroth condenser, a dropping funnel and a stirring bar, 300 mL of 2-pentanol and 30 g of potassium hydroxide (manufactured by Wako Pure Chemical Industries, Ltd., purity: approximately 85%) were charged, and the resulting mixture was stirred for approximately 2.5 hours at 50° C. When potassium hydroxide was dissolved to produce a uniform solution, 81 g of methyl p-toluenesulfonate was added from a dropping funnel to the uniform solution over approximately 1 hour, and the resulting mixture was stirred at 50° C. for a little over 3 hours. The reaction mixture was cooled to room temperature, and the content was transferred into a beaker; water was added to the beaker, and thus the produced potassium p-toluenesulfonate was dissolved. The solution in the beaker was transferred into a separating funnel, the aqueous layer was separated, and thus a liquid mixture composed of 2-pentyl methyl ether and 2-pentanol was obtained.

The obtained liquid mixture was charged in a distillation still, and distilled by using a KS-type rectifier (manufactured by TOKA SEIKI Co., Ltd., column length: 30 cm, column packing material: Helipack No. 1). The fraction of the column top temperature of 74-75° C. was collected, the water azeotropically boiled and distilled was separated by using a separating funnel, the obtained distillate was dried with the molecular sieves 4A, and thus 16 g of 2-pentyl methyl ether was obtained (yield: 37%).
GC-MS (EI-MS): m/z 87, 71, 59, 45

[Production Example 4] Production of Acetyl Fluoride

In a 500 mL volume glass reactor equipped with a stirrer, a dropping funnel and a collection trap, 200 mL of acetic anhydride and 46.9 g of potassium hydrogen difluoride were charged, and the resulting mixture was stirred while being heated to 40° C. To the mixture, 47 g of acetyl chloride was dropwise added from the dropping funnel over 40 minutes, and after the completion of the dropwise addition, the temperature of the reactor was increased by 10° C. every 15 minutes. The reactor was finally heated to 90° C., and then maintained at that temperature for 20 minutes, and subsequently the reaction was terminated. Acetyl fluoride distilled from the reactor during the reaction was collected in a glass trap cooled with ice water. The crude product amount was 47.6 g (crude yield: 128%). In the present reaction, acetyl fluoride is also produced from acetic anhydride, and accordingly the yield exceeds 100%.

The obtained crude acetyl fluoride was subjected to a simple distillation, the fraction of the column top temperature of 20-24° C. was collected, and thus 42.4 g of acetyl fluoride was obtained (yield: 114%).

[Production Example 5] Production of Propionyl Fluoride

In a 500 mL volume glass reactor equipped with a stirrer, a dropping funnel and a collection trap, 200 mL of propionic anhydride and 46.8 g of potassium hydrogen difluoride were charged, and the resulting mixture was stirred while being heated to 90° C. To the mixture, 55.5 g of propionyl chloride was dropwise added from the dropping funnel over 1 hour, and after the completion of the dropwise addition, the mixture was further stirred for 15 minutes. Subsequently, the temperature of the reactor was increased by 10° C. every 15 minutes, so as to heat the reactor up to 110° C. The resulting mixture was stirred at 110° C. for 30 minutes, and then the reaction was terminated. Propionyl fluoride distilled from the reactor during the reaction was collected in a glass trap cooled with ice water. The crude yield was 132%. In the present reaction, propionyl fluoride is also produced from propionic anhydride, and accordingly the yield exceeds 100%.

The obtained crude propionyl fluoride was subjected to a simple distillation, the fraction of the column top temperature of 42-43° C. was collected, and thus 46.8 g of propionyl fluoride was obtained (yield: 103%).

Example 1

In a 50 mL volume glass reactor equipped with a stirring bar and a Dimroth condenser (circulating a coolant of 0° C.), 1.76 g of sec-butyl methyl ether synthesized in Production Example 1 and 5 mL of dry n-hexane were charged, under nitrogen atmosphere, and the resulting mixture was cooled to 0° C. To the cooled mixture, 2.48 g of acetyl fluoride synthesized in Production Example 4 was added, and the resulting mixture was stirred and further added with 0.094 g of lithium tetrafluoroborate (manufactured by Wako Pure Chemical Industries, Ltd.). The mixture was stirred at 0° C. for 30 minutes and then the temperature was increased to 20° C., and the content was stirred for another 6.5 hours. After the stirring was stopped, the mixture was left to stand, so as to obtain a gray precipitate and a colorless solution.

After the completion of the reaction, the reaction mixture was analyzed by GC, and consequently it was found that sec-butyl methyl ether, the raw material, was substantially disappeared, 2-fluorobutane, the target compound, was produced in 8.87 area %, and 1-butene, (E)-2-butene, and (Z)-2-butene were produced in 0.14 area %, 4.22 area %, and 2.71 area %, respectively. In addition, 2-acetoxybutane (raw material derived component) attributable to the acetoxylation of the raw material was produced in 3.84 area %. The remainder was composed of n-hexane, the solvent, and methyl acetate resulting from the reaction.

The reaction liquid was filtered through a PTFE membrane filter (pore size: 0.2 μm) so as to remove precipitate (catalyst residue), to thereby recover a colorless transparent solution.

Example 2

A reaction was performed in the same manner as in Example 1, except that 0.094 g of lithium tetrafluoroborate as the catalyst was replaced with 0.028 g of lithium fluoride.

After the completion of the reaction, the reaction mixture was analyzed by GC, and consequently it was found that sec-butyl methyl ether, the raw material, was substantially disappeared, 2-fluorobutane, the target compound, was produced in 16.73 area %, and 1-butene, (E)-2-butane, and (Z)-2-butane were produced in 0.12 area %, 4.69 area %, and 1.96 area %, respectively. In addition, 2-acetoxybutane attributable to the acetoxylation of the raw material was produced in 2.00 area %. The remainder was composed of n-hexane, the solvent, and methyl acetate resulting from the reaction.

Examples 3-5

A reaction was performed in the same manner as in Example 1, except that 0.094 g of lithium tetrafluoroborate as the catalyst was replaced with: 0.046 g of lithium chloride; 0.088 g of lithium bromide; and 0.136 g of lithium iodide, respectively. When lithium bromide or lithium iodide was used, 2-bromobutane and 2-iodobutane as halogen exchangers were by-produced in 0.15 area % and 1.18 area %, respectively, in addition to 2-acetoxybutane attributable to the acetoxylation of the raw material. The reaction results are summarized in Table 1.

Example 6

A reaction was performed in the same manner as in Example 1, except that 0.094 g of lithium tetrafluoroborate as the catalyst was replaced with 0.069 g of lithium nitrate, and further the stirring time at 20° C. was changed from 6.5 hours to 7 hours. After the completion of the reaction, the reaction mixture was analyzed by GC, and consequently it was found that sec-butyl methyl ether, the raw material, was produced in 1.41 area %, 2-fluorobutane, the target compound, was produced in 15.03 area %, and 1-butene, (E)-2-butene, and (Z)-2-butene were produced in 0.11 area %, 4.40 area %, and 1.77 area %, respectively. In addition, 2-acetoxybutane attributable to the acetoxylation of the raw material was produced in 2.36 area %. The remainder was composed of n-hexane, the solvent, and methyl acetate resulting from the reaction.

Examples 7-9

A reaction was performed in the same manner as in Example 1, except that 0.094 g of lithium tetrafluoroborate as the catalyst was replaced with: 0.037 g of lithium carbonate; 0.039 g of lithium phosphate; and 0.103 g of lithium sulfamate, respectively. The reaction results are summarized in Table 1.

Examples 10-14, and 16

A reaction was performed in the same manner as in Example 1, except that 0.094 g of lithium tetrafluoroborate as the catalyst was replaced with: 0.066 g of lithium acetate; 0.064 g of lithium maleate; 0.051 g of lithium oxalate; 0.102 g of lithium methanesulfonate; 0.178 g of lithium p-toluene sulfonate; and 0.306 g of lithium nonafluorobutanesulfonate, respectively. The reaction results are summarized in Table 1.

Example 15

A reaction was performed in the same manner as in Example 1, except that 0.094 g of lithium tetrafluoroborate as the catalyst was replaced with 0.156 g of lithium trifluoromethanesulfonate, and further the stirring time at 20° C. was changed to 7.5 hours. After the completion of the reaction, the reaction mixture was analyzed by GC, and consequently it was found that sec-butyl methyl ether, the raw material, was produced in 2.09 area %, 2-fluorobutane, the target compound, was produced in 10.76 area %, and 1-butene, (E)-2-butene, and (Z)-2-butene were produced in 0.28 area %, 7.54 area %, and 3.29 area %, respectively. In addition, 2-acetoxybutane attributable to the acetoxylation of the raw material was produced in 2.61 area %. The remainder was composed of n-hexane, the solvent, and methyl acetate resulting from the reaction.

Example 17

In a 50 mL volume glass reactor equipped with a Dimroth condenser (circulating a coolant of 0° C.), 1.76 g of sec-butyl methyl ether synthesized in Production Example 1 and 5 mL of dry n-hexane were charged, under nitrogen atmosphere, and the resulting mixture was cooled to 0° C. To the cooled mixture, 2.48 g of acetyl fluoride synthesized in Production Example 4 was added, and the resulting mixture was stirred and further added with 0.11 g of sodium tetrafluoroborate (manufactured by Wako Pure Chemical Industries, Ltd.). The mixture was stirred at 0° C. for 30 minutes and then the temperature was increased to 20° C., and the content was stirred for another 6.5 hours. After the stirring was stopped, the mixture was left to stand, so as to obtain a gray precipitate and a colorless solution.

After the completion of the reaction, the reaction mixture was analyzed by GC, and consequently it was found that sec-butyl methyl ether, the raw material, was substantially disappeared, 2-fluorobutane, the target compound, was produced in 12.61 area %, and 1-butene, (E)-2-butene, and (Z)-2-butene were produced in 0.13 area %, 5.62 area %, and 1.95 area %, respectively. In addition, 2-acetoxybutane (raw material derived component) attributable to the acetoxylation of the raw material was produced in 2.25 area %. The remainder was composed of n-hexane, the solvent, and methyl acetate resulting from the reaction.

The reaction liquid is filtered by PTFE membrane filter (pore size: 0.2 μm) so as to remove precipitate (catalyst residue), to thereby recover a colorless transparent solution.

Examples 18-19

A reaction was performed in the same manner as in Example 17, except that 0.11 g of sodium tetrafluoroborate as the catalyst was replaced with: 0.042 g of sodium fluoride; and 0.102 g of sodium bromide, respectively. The reaction results are summarized in Table 1.

Example 20

A reaction was performed in the same manner as in Example 17, except that 0.11 g of sodium tetrafluoroborate as the catalyst was replaced with 0.15 g of sodium iodide, and further the stirring time at 20° C. was changed to 5.5 hours. After the completion of the reaction, the reaction mixture was analyzed by GC, and consequently it was found that that sec-butyl methyl ether, the raw material, was substantially disappeared, 2-fluorobutane, the target compound, was produced in 13.34 area %, and 1-butene, (E)-2-butene, and (Z)-2-butene were produced in 0.21 area %, 5.72 area %, and 2.29 area %, respectively. In addition, 2-acetoxybutane attributable to the acetoxylation of the raw material was produced in 2.40 area %, and 2-iodinebutane was produced 1.35 area %. The remainder was composed of n-hexane, the solvent, and methyl acetate resulting from the reaction.

Examples 21, 23-25

A reaction was performed in the same manner as in Example 17, except that 0.11 g of sodium tetrafluoroborate as the catalyst was replaced with: 0.168 g of sodium hexafluorophosphate; 0.062 g of sodium hydrogen difluoride; 0.119 g of sodium sulfamate, and 0.084 g of sodium hydrogen carbonate. The reaction results are summarized in Table 1.

Example 22

A reaction was performed in the same manner as in Example 17, except that 0.11 g of sodium tetrafluoroborate as the catalyst was replaced with 0.085 g of sodium nitrate, and further the stirring time at 20° C. was changed to 7 hours. After the completion of the reaction, the reaction mixture was analyzed by GC, and consequently it was found that that sec-butyl methyl ether, the raw material, was substantially disappeared, 2-fluorobutane, the target compound, was produced in 14.63 area %, and 1-butene, (E)-2-butene, and (Z)-2-butene were produced in 0.14 area %, 4.73 area %, and 2.02 area %, respectively. In addition, 2-acetoxybutane attributable to the acetoxylation of the raw material was produced in 2.58 area %. The remainder was composed of n-hexane, the solvent, and methyl acetate resulting from the reaction.

Example 26

A reaction was performed in the same manner as in Example 17, except that 0.11 g of sodium tetrafluoroborate as the catalyst was replaced with 0.104 g of sodium hydrogen sulfite, and further the stirring time at 20° C. was changed to 7 hours. After the completion of the reaction, the reaction mixture was analyzed by GC, and consequently it was found that that sec-butyl methyl ether, the raw material, was substantially disappeared, 2-fluorobutane, the target compound, was produced in 14.21 area %, and 1-butene, (E)-2-butene, and (Z)-2-butene were produced in 0.12 area %, 4.46 area %, and 2.04 area %, respectively. In addition, 2-acetoxybutane attributable to the acetoxylation of the raw material was produced in 2.36 area %. The remainder was composed of n-hexane, the solvent, and methyl acetate resulting from the reaction.

Examples 27-40

A reaction was performed in the same manner as in Example 17, except that 0.11 g of sodium tetrafluoroborate as the catalyst was replaced with 0.063 g of sodium sulfite, 0.071 g of sodium sulfate, 0.053 g of sodium carbonate, 0.055 of sodium phosphate, 0.087 g of sodium thiosulfate, 0.082 g of sodium acetate, 0.068 g of sodium formate, 0.067 g of sodium oxalate, 0.08 g of sodium maleate, 0.118 g of sodium methanesulfonate, 0.194 g of sodium p-toluenesulfonate, 0.136 g of sodium trifluoroacetate, 0.236 g of sodium heptafluorobutyrate, and 0.172 g of sodium trifluoromethanesulfonate. The reaction results are summarized in Table 1.

Example 41

A reaction was performed in the same manner as in Example 17, except that n-hexane as the solvent was changed to n-heptane. After the completion of the reaction, the reaction mixture was analyzed by GC, and consequently it was found that that sec-butyl methyl ether, the raw material, was substantially disappeared, 2-fluorobutane, the target compound, was produced in 9.57 area %, and 1-butene, (E)-2-butene, and (Z)-2-butene were produced in 0.13 area %, 5.82 area %, and 2.13 area %, respectively. In addition, 2-acetoxybutane attributable to the acetoxylation of the raw material was produced in 2.55 area %. The remainder was composed of n-heptane, the solvent, and methyl acetate resulting from the reaction.

Example 42

A reaction was performed in the same manner as in Example 17, except that n-hexane as the solvent was changed to cyclohexane. After the completion of the reaction, the reaction mixture was analyzed by GC, and consequently it was found that that sec-butyl methyl ether, the raw material, was substantially disappeared, 2-fluorobutane, the target compound, was produced in 11.75 area %, and 1-butene, (E)-2-butene, and (Z)-2-butene were produced in 0.15 area %, 6.36 area %, and 2.18 area %, respectively. In addition, 2-acetoxybutane attributable to the acetoxylation of the raw material was produced in 2.01 area %. The remainder was composed of cyclohexane, the solvent, and methyl acetate resulting from the reaction.

Example 43

A reaction was performed in the same manner as in Example 17, except that 2.48 g of acetyl fluoride was changed to 3.04 g propionyl fluoride synthesized in Production Example 5. After the completion of the reaction, the reaction mixture was analyzed by GC, and consequently it was found that that sec-butyl methyl ether, the raw material, was substantially disappeared, 2-fluorobutane, the target compound, was produced in 8.21 area %, and 1-butene, (E)-2-butene, and (Z)-2-butene were produced in 0.14 area %, 6.43 area %, and 2.17 area %, respectively. In addition, 2-propionyloxybutane attributable to the propionyloxylation of the raw material was produced in 3.98 area %. The remainder was composed of n-hexane, the solvent, and methyl propionate resulting from the reaction.

Example 44

A reaction was performed in the same manner as in Example 17, except that 1.76 g of sec-butyl methyl ether as the raw material was changed to 2.04 g of sec-pentyl methyl ether, and n-hexane as the solvent was changed to n-heptane. After the completion of the reaction, the reaction mixture was analyzed by GC, and consequently it was found that that 2-pentyl methyl ether, the raw material, was disappeared, 2-fluoropentane, the target compound, was produced in 9.34 area %, and 3-fluoropentane was produced in 4.47 area % and pentene as an isomer mixture was produced in 8.28 area %. In addition, 2-acetoxypentane attributable to the acetoxylation of the raw material was produced in 2.34 area %.

Example 45

A reaction was performed in the same manner as in Example 17, except that 1.76 g of sec-butyl methyl ether as the raw material was changed to 2.04 g of sec-butyl ethyl ether synthesized in Production Example 2. After the completion of the reaction, the reaction mixture was analyzed by GC, and consequently it was found that sec-butyl ethyl ether, the raw material, was substantially disappeared, 2-fluorobutane, the target compound, was produced in 11.04 area %, and 1-butene, (E)-2-butene, and (Z)-2-butene were produced in 0.12 area %, 3.82 area %, and 1.31 area %, respectively. In addition, 2-acetoxybutane attributable to the acetoxylation of the raw material was produced only in 3.52 area %.

Example 46

A reaction was performed in the same manner as in Example 17, except that 1.76 g of sec-butyl methyl ether as the raw material was changed to 1.76 g of t-butyl methyl ether. After the completion of the reaction, the reaction mixture was analyzed by GC, and consequently it was found that t-butyl methyl ether, the raw material, remained in 1.34 area %, t-butyl fluoride, the target compound, was produced in 15.11 area %, and isobutene in 1.58 area %. In addition, t-butyl acetate attributable to the acetoxylation of the raw material was produced only in 1.93 area %.

Example 47

A reaction was performed in the same manner as in Example 17, except that 1.76 g of sec-butyl methyl ether as the raw material was changed to 2.04 g of t-butyl ethyl ether. After the completion of the reaction, the reaction mixture was analyzed by GC, and consequently it was found that t-butyl ethyl ether, the raw material, was substantially disappeared, t-butyl fluoride, the target compound, was produced in 17.96 area %, and isobutene in 1.45 area %. In addition, t-butyl acetate attributable to the acetoxylation of the raw material was produced in 1.48 area %.

Comparative Example 1

In a 50 mL volume glass reactor equipped with a stirring bar and a Dimroth condenser, 3.52 g of sec-butyl methyl ether synthesized in Production Example 1, 2.98 g of acetyl fluoride synthesized in Production Example 4, and 10 mL of n-hexane were charged, and the resulting mixture was cooled to 0° C. and the content was stirred. To the cooled mixture, 2.48 g of boron trifluoride tetrahydrofuran complex was added by means of a syringe, and the resulting mixture was stirred for 3 hours while being held at 0° C.

The content was analyzed by GC, and consequently it was found that sec-butyl methyl ether, the raw material, was substantially disappeared, 2-fluorobutane, the target compound, was produced in 24.45 area %, and 1-butene, (E)-2-butene, and (Z)-2-butene were produced in 0.18 area %, 6.50 area %, and 2.00 area %, respectively. In addition, 2-acetoxybutane attributable to the acetoxylation of the raw material was produced in 0.35 area %. The remainder was composed of n-hexane, the solvent, and tetrahydrofuran derived from the complex, and methyl acetate. The reaction liquid was dark brown.

The results of Examples 1-47 and Comparative Example 1 are summarized in Table 1 below.

In Table 1, Ts represents 4-methylphenylsulfonyl.

TABLE 1

| | Ether Compound (1) | Acid Fluoride (2) | Catalyst | Solvent | Reaction Time (h) |
|---|---|---|---|---|---|
| Example 1 | sec-butyl methyl ether | acetyl fluoride | $LiBF_4$ | n-hexane | 7 |
| Example 2 | sec-butyl methyl ether | acetyl fluoride | LiF | n-hexane | 7 |
| Example 3 | sec-butyl methyl ether | acetyl fluoride | LiCl | n-hexane | 7 |
| Example 4 | sec-butyl methyl ether | acetyl fluoride | LiBr | n-hexane | 7 |
| Example 5 | sec-butyl methyl ether | acetyl fluoride | LiI | n-hexane | 7 |
| Example 6 | sec-butyl methyl ether | acetyl fluoride | $LiNO_3$ | n-hexane | 7.5 |
| Example 7 | sec-butyl methyl ether | acetyl fluoride | $Li_2CO_3$ | n-hexane | 7 |
| Example 8 | sec-butyl methyl ether | acetyl fluoride | $Li_3PO_4$ | n-hexane | 7 |
| Example 9 | sec-butyl methyl ether | acetyl fluoride | $H_2NSO_3Li$ | n-hexane | 7 |
| Example 10 | sec-butyl methyl ether | acetyl fluoride | $CH_3CO_2Li$ | n-hexane | 7 |
| Example 11 | sec-butyl methyl ether | acetyl fluoride | $LiO_2CC\!=\!CCO_2Li$ | n-hexane | 7 |
| Example 12 | sec-butyl methyl ether | acetyl fluoride | $(CO_2Li)_2$ | n-hexane | 7 |
| Example 13 | sec-butyl methyl ether | acetyl fluoride | $CH_3SO_3Li$ | n-hexane | 7 |
| Example 14 | sec-butyl methyl ether | acetyl fluoride | TsOLi | n-hexane | 7 |
| Example 15 | sec-butyl methyl ether | acetyl fluoride | $CF_3SO_3Li$ | n-hexane | 8 |
| Example 16 | sec-butyl methyl ether | acetyl fluoride | $C_4F_9SO_3Li$ | n-hexane | 7 |
| Example 17 | sec-butyl methyl ether | acetyl fluoride | $NaBF_4$ | n-hexane | 7 |
| Example 18 | sec-butyl methyl ether | acetyl fluoride | NaF | n-hexane | 7 |
| Example 19 | sec-butyl methyl ether | acetyl fluoride | NaBr | n-hexane | 7 |
| Example 20 | sec-butyl methyl ether | acetyl fluoride | NaI | n-hexane | 6 |
| Example 21 | sec-butyl methyl ether | acetyl fluoride | $NaPF_6$ | n-hexane | 7 |
| Example 22 | sec-butyl methyl ether | acetyl fluoride | $NaNO_3$ | n-hexane | 7.5 |
| Example 23 | sec-butyl methyl ether | acetyl fluoride | $NaHF_2$ | n-hexane | 7 |
| Example 24 | sec-butyl methyl ether | acetyl fluoride | $H_2NSO_3Na$ | n-hexane | 7 |
| Example 25 | sec-butyl methyl ether | acetyl fluoride | $NaHCO_3$ | n-hexane | 7 |
| Example 26 | sec-butyl methyl ether | acetyl fluoride | $NaHSO_3$ | n-hexane | 7.5 |
| Example 27 | sec-butyl methyl ether | acetyl fluoride | $Na_2SO_3$ | n-hexane | 7 |
| Example 28 | sec-butyl methyl ether | acetyl fluoride | $Na_2SO_4$ | n-hexane | 7 |
| Example 29 | sec-butyl methyl ether | acetyl fluoride | $Na_2CO_3$ | n-hexane | 7 |
| Example 30 | sec-butyl methyl ether | acetyl fluoride | $Na_3PO_4$ | n-hexane | 7 |
| Example 31 | sec-butyl methyl ether | acetyl fluoride | $Na_2S_2O_4$ | n-hexane | 7 |
| Example 32 | sec-butyl methyl ether | acetyl fluoride | $CH_3CO_2Na$ | n-hexane | 7 |
| Example 33 | sec-butyl methyl ether | acetyl fluoride | $HCO_2Na$ | n-hexane | 7 |
| Example 34 | sec-butyl methyl ether | acetyl fluoride | $(CO_2Na)_2$ | n-hexane | 7 |
| Example 35 | sec-butyl methyl ether | acetyl fluoride | $NaO_2CC\!=\!CCO_2Na$ | n-hexane | 7 |
| Example 36 | sec-butyl methyl ether | acetyl fluoride | $CH_3SO_3Na$ | n-hexane | 7 |
| Example 37 | sec-butyl methyl ether | acetyl fluoride | TsONa | n-hexane | 7 |
| Example 38 | sec-butyl methyl ether | acetyl fluoride | $CF_3CO_2Na$ | n-hexane | 7 |

TABLE 1-continued

| | | | | | |
|---|---|---|---|---|---|
| Example 39 | sec-butyl methyl ether | acetyl fluoride | $C_3F_7CO_2Na$ | n-hexane | 7 |
| Example 40 | sec-butyl methyl ether | acetyl fluoride | $CF_3SO_3Na$ | n-hexane | 7 |
| Example 41 | sec-butyl methyl ether | acetyl fluoride | $NaBF_4$ | n-heptane | 7 |
| Example 42 | sec-butyl methyl ether | acetyl fluoride | $NaBF_4$ | cyclohexane | 7 |
| Example 43 | sec-butyl methyl ether | propionyl fluoride | $NaBF_4$ | n-hexane | 7 |
| Example 44 | 2-pentyl methyl ether | acetyl fluoride | $NaBF_4$ | n-heptane | 7 |
| Example 45 | sec-butyl methyl ether | acetyl fluoride | $NaBF_4$ | n-hexane | 7 |
| Example 46 | t-butyl methyl ether | acetyl fluoride | $NaBF_4$ | n-hexane | 7 |
| Example 47 | t-butyl methyl ether | acetyl fluoride | $NaBF_4$ | n-hexane | 7 |
| Comparative Exampple 1 | sec-butyl methyl ether | acetyl fluoride | $BF_3 \cdot THF$ | n-hexane | 3 |

| | Product (area %) | | | | | | | | |
|---|---|---|---|---|---|---|---|---|---|
| | Target | 1-Butene | (E)-2-Butene | (Z)-2-Butene | 3-Fluoro Pentane | Pentene | Isobutene | Raw Material-Derived Component | Halogen Exchanger | Raw Material |
| Example 1 | 8.87 | 0.14 | 4.22 | 2.71 | | | | 3.84 | | ≈0 |
| Example 2 | 16.73 | 0.12 | 4.69 | 1.96 | | | | 2.00 | | ≈0 |
| Example 3 | 13.12 | 0.11 | 4.09 | 1.82 | | | | 2.31 | | ≈0 |
| Example 4 | 12.26 | 0.14 | 4.71 | 2.25 | | | | 3.21 | 0.15 | ≈0 |
| Example 5 | 12.98 | 0.18 | 5.01 | 2.23 | | | | 2.33 | 1.18 | ≈0 |
| Example 6 | 15.03 | 0.11 | 4.40 | 1.77 | | | | 2.36 | | 1.41 |
| Example 7 | 12.64 | 0.15 | 5.55 | 2.23 | | | | 2.94 | | ≈0 |
| Example 8 | 15.02 | 0.14 | 4.96 | 2.13 | | | | 1.56 | | ≈0 |
| Example 9 | 14.18 | 0.13 | 4.39 | 1.99 | | | | 2.32 | | ≈0 |
| Example 10 | 13.06 | 0.11 | 4.15 | 1.88 | | | | 2.95 | | ≈0 |
| Example 11 | 16.54 | 0.14 | 4.83 | 2.05 | | | | 2.23 | | ≈0 |
| Example 12 | 11.57 | 0.09 | 3.56 | 1.57 | | | | 2.09 | | 3.35 |
| Example 13 | 14.54 | 0.18 | 6.26 | 2.70 | | | | 1.97 | | ≈0 |
| Example 14 | 13.68 | 0.11 | 4.09 | 1.76 | | | | 2.79 | | 1.63 |
| Example 15 | 10.76 | 0.28 | 7.54 | 3.29 | | | | 2.61 | | 2.09 |
| Example 16 | 12.93 | 0.23 | 6.46 | 2.90 | | | | 2.64 | | ≈0 |
| Example 17 | 12.61 | 0.13 | 5.62 | 1.95 | | | | 2.25 | | ≈0 |
| Example 18 | 15.23 | 0.18 | 6.27 | 2.29 | | | | 2.17 | | 1.79 |
| Example 19 | 12.83 | 0.13 | 4.79 | 2.08 | | | | 2.88 | | ≈0 |
| Example 20 | 13.34 | 0.21 | 5.72 | 2.29 | | | | 2.40 | 1.35 | ≈0 |
| Example 21 | 8.83 | 0.25 | 6.34 | 3.59 | | | | 2.73 | | ≈0 |
| Example 22 | 14.63 | 0.14 | 4.73 | 2.02 | | | | 2.58 | | ≈0 |
| Example 23 | 13.28 | 0.11 | 4.16 | 1.89 | | | | 2.81 | | 1.17 |
| Example 24 | 16.14 | 0.17 | 5.30 | 2.29 | | | | 1.89 | | 1.81 |
| Example 25 | 13.25 | 0.15 | 5.26 | 1.84 | | | | 2.76 | | 2.71 |
| Example 26 | 14.21 | 0.12 | 4.46 | 2.04 | | | | 2.36 | | ≈0 |
| Example 27 | 14.02 | 0.16 | 5.35 | 2.22 | | | | 1.96 | | ≈0 |
| Example 28 | 13.32 | 0.18 | 6.04 | 2.32 | | | | 2.53 | | ≈0 |
| Example 29 | 14.12 | 0.11 | 4.23 | 1.93 | | | | 2.39 | | ≈0 |
| Example 30 | 13.95 | 0.10 | 3.78 | 1.67 | | | | 1.97 | | 1.75 |
| Example 31 | 13.22 | 0.11 | 3.72 | 1.61 | | | | 1.67 | | 4.73 |
| Example 32 | 14.30 | 0.15 | 5.06 | 2.22 | | | | 2.05 | | ≈0 |
| Example 33 | 11.05 | 0.08 | 2.77 | 1.13 | | | | 1.42 | | 8.99 |
| Example 34 | 11.60 | 0.09 | 3.33 | 1.33 | | | | 1.36 | | 7.98 |
| Example 35 | 13.61 | 0.17 | 5.60 | 2.56 | | | | 2.60 | | ≈0 |
| Example 36 | 12.49 | 0.12 | 4.40 | 1.89 | | | | 2.41 | | 1.49 |
| Example 37 | 11.43 | 0.10 | 3.53 | 1.46 | | | | 1.70 | | 5.57 |
| Example 38 | 12.16 | 0.13 | 5.24 | 2.06 | | | | 2.88 | | ≈0 |
| Example 39 | 13.47 | 0.11 | 4.08 | 1.69 | | | | 1.74 | | 3.45 |
| Example 40 | 12.99 | 0.17 | 5.21 | 2.52 | | | | 2.81 | | ≈0 |
| Example 41 | 9.57 | 0.13 | 5.82 | 2.13 | | | | 2.55 | | ≈0 |
| Example 42 | 11.75 | 0.15 | 6.36 | 2.18 | | | | 2.01 | | ≈0 |
| Example 43 | 8.21 | 0.14 | 6.43 | 2.17 | | | | 3.98 | | ≈0 |
| Example 44 | 9.34 | | | | 4.47 | 8.28 | | 2.34 | | ≈0 |
| Example 45 | 11.04 | 0.12 | 3.82 | 1.31 | | | | 3.52 | | ≈0 |
| Example 46 | 15.11 | | | | | | 1.58 | 1.93 | | 1.34 |
| Example 47 | 17.96 | | | | | | 1.45 | 1.48 | | ≈0 |
| Comparative Exampple 1 | 24.45 | 0.18 | 6.50 | 2.00 | | | | 0.35 | | ≈0 |

The followings can be found from the aforementioned results.

In Examples where lithium salt or sodium salt was used as the catalyst, no ether compound is by-produced, the catalyst residue is removable through mere filtering after the reaction, and a substantially colorless reaction liquid is recovered.

On the other hand, in Comparative Example 1 where boron trifluoride tetrahydrofuran complex was used as the catalyst, tetrahydrofuran (ether compound (impurities)) liberated from the catalyst remains in the reaction liquid. The removal of boron trifluoride tetrahydrofuran complex, which is a liquid, requires post-treatment operation such as neutralization after the completion of reaction, which makes the operation cumbersome. Further, the reaction liquid thus obtained was dark-browned.

According to the disclosed method, the resulting reaction liquid is substantially colorless, and the post-treatment after the reaction is simple, which allows for industrially advantageous manufacture of fluorinated hydrocarbon such as 2-fluorobutane.

The invention claimed is:

1. A method for producing a fluorinated hydrocarbon represented by formula (3) below, wherein an ether compound represented by formula (1) below and an acid fluoride represented by formula (2) below are brought into contact with each other in a hydrocarbon-based solvent, in the presence of lithium salt or sodium salt,

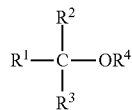 (1)

(in formula (1) above, $R^1$ and $R^2$ each independently represent an alkyl group having 1 to 3 carbon atoms, $R^3$ represents a hydrogen atom, a methyl group or an ethyl group, and $R^4$ represents a methyl group or an ethyl group; and $R^1$ and $R^2$ may be bonded to each other to form a cyclic structure), $$R^5\text{—COF} \qquad (2)$$

(in formula (2) above, $R^5$ represents a methyl group or an ethyl group),

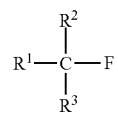 (3)

(in formula (3) above, $R^1$ to $R^3$ represent the same meanings as described above).

2. The production method according to claim 1, wherein the lithium salt or the sodium salt is inorganic acid salt.

3. The production method according to claim 1, wherein the ether compound represented by the formula (1) is sec-butyl methyl ether or t-butyl methyl ether.

4. The production method according to claim 1, wherein the acid fluoride represented by the formula (2) is acetyl fluoride.

5. The production method according to claim 1, wherein the fluorinated hydrocarbon represented by the formula (3) is 2-fluorobutane.

* * * * *